United States Patent [19]
Amplatz et al.

[11] Patent Number: 5,171,233
[45] Date of Patent: Dec. 15, 1992

[54] SNARE-TYPE PROBE

[75] Inventors: Kurt Amplatz, St. Paul; Frank Kotula, Maple Grove; Rudy A. Mazzocchi, Woodbury, all of Minn.

[73] Assignee: Microvena Corporation, Vadnais Heighst, Minn.

[21] Appl. No.: 514,137

[22] Filed: Apr. 25, 1990

[51] Int. Cl.⁵ ............................................. A61M 25/00
[52] U.S. Cl. .................................. 604/281; 606/113; 606/127
[58] Field of Search ............... 606/127, 113, 198, 108, 606/109; 128/840, 838; 604/281

[56] References Cited

U.S. PATENT DOCUMENTS

| | | | |
|---|---|---|---|
| 1,225,771 | 5/1917 | Clare | 606/113 |
| 3,828,790 | 8/1974 | Curtiss et al. | 606/113 |
| 3,868,956 | 3/1975 | Alfidi et al. | |
| 4,425,908 | 1/1984 | Simon | |
| 4,503,569 | 3/1985 | Dotter | |
| 4,512,338 | 4/1985 | Balko et al. | 606/108 |
| 4,576,162 | 3/1986 | McCorkle | 128/419 P |
| 4,779,616 | 10/1988 | Johnson | |
| 4,840,176 | 6/1989 | Ohno | 606/127 |
| 4,849,032 | 7/1989 | Kawaguchi | |
| 4,950,258 | 8/1990 | Kawai et al. | 604/281 |
| 4,991,602 | 2/1991 | Amplatz et al. | |
| 5,057,114 | 10/1991 | Wittich et al. | 606/127 |
| 5,064,428 | 11/1991 | Cope et al. | 606/127 |

FOREIGN PATENT DOCUMENTS

| | | | |
|---|---|---|---|
| 2540818 | 4/1976 | Denmark | 606/113 |
| 3804849 | 9/1988 | Denmark | 606/113 |
| 0027704 | 4/1981 | European Pat. Off. | 606/113 |
| 0724776 | 5/1932 | France | 606/113 |

OTHER PUBLICATIONS

Curry, "Retrieval of Detached Intravascular Catheter or Guide Fragments—A Proposed Method," 105 Amer. Jour. of Roentgenology, (1969), pp. 894–896.
Tatsumi et al., "Retrieval of a Ventriculoatrial Shung Catheter from the Heart by a Venous Catheterization Technique," 32 Jour. of Neurosurgery, (1970), pp. 593–595.
Bloomfield, "The Nonsurgical Retrieval of Itracardiac Foreign Bodies-An International Survey," for *Catheterization and Cardiovascular Diagnosis* (1978), 1–14.
1986 Product Catalog, distributed by the Cook Company, p. 2.

*Primary Examiner*—C. Fred Rosenbaum
*Assistant Examiner*—William W. Lewis
*Attorney, Agent, or Firm*—Fredrikson & Byron

[57] ABSTRACT

The present invention provides a snare for intravascular use having an elongate proximal member and a loop-shaped distal segment oriented at an angle to the adjacent portion of the proximal member. The snare may be formed of a superelastic shape memory alloy, which permits the distal segment to be collapsed for passage through a catheter and yet automatically open into its original, unrestrained configuration upon emerging from the distal tip of the catheter.

16 Claims, 2 Drawing Sheets

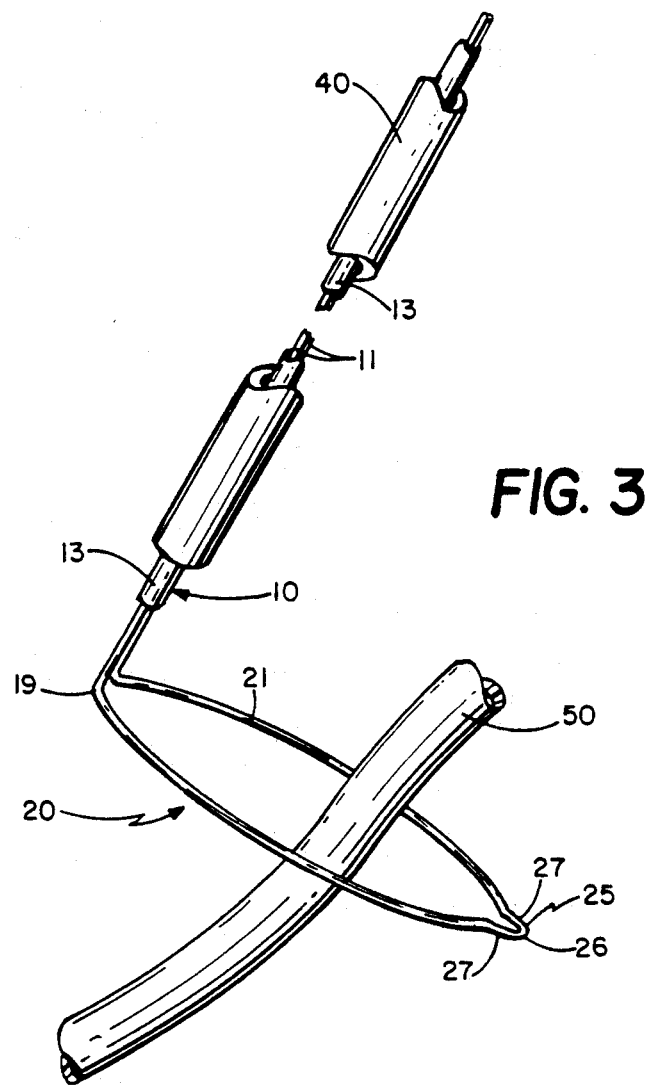
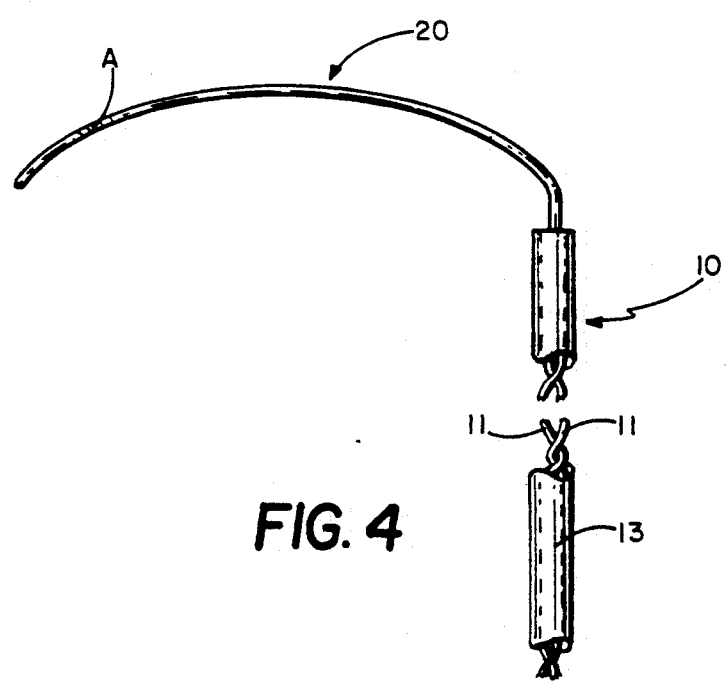

SNARE-TYPE PROBE

FIELD OF THE INVENTION

The present invention generally relates to devices used in medical procedures and has particular utility for retrieving items from cavities within the body.

BACKGROUND OF THE INVENTION

During medical procedures which utilize catheters and guide wires, a distal portion of the catheter or guide wire can sometimes accidentally detach from the rest of the article and be left within the patient. This fragment may then travel, e.g., within the vascular system until it comes to rest either within a vein or artery, usually at a branching point, or in a body cavity, such as the heart. The results of leaving these foreign bodies within a patient can be quite harmful, and include septicemia, multiple pulmonary emboli, perforation, and even sudden death.

In the past, foreign articles were often left in place despite these grave risks because the procedural options for removal were highly traumatic. The risks associated with open heart surgery to remove items lodged in the heart, for example, may well outweigh the problems inherent in allowing the article to remain.

Safer techniques were then developed to remove foreign objects from the body. These techniques use a grasping mechanism carried within a catheter to grip the foreign object and retract it to a more accessible location or even out of the patient through the catheter's site of entry.

Three basic configurations of grasping mechanisms are most commonly employed: a modified urological stone basket, rigid forceps, and a snare comprising a loop of wire extending from the forward end of a catheter. The stone basket technique utilizes an assembly of a plurality of wires within a sheath, the assembly being threaded through a catheter. The wires are all joined at their distal end and, when the wires protrude beyond the tip of the sheath, the wires become spaced away from one another to define a wire "basket." The basket is closed by retracting the wires within the sheath and opened by advancing the wires through the tip of the sheath Forceps used in these types of operations are much like those used in bronchoscopic procedures and comprise a pair of rigid fingers which may be urged toward one another to pinch the object therebetween. Use of these devices is limited almost exclusively to items lodged in relatively large cavities such as the right atrium or venacava. Although this instrument has one major advantage in that it may grasp the item to be retrieved at any point, the rigidity of the instrument limits maneuverability and creates a risk of perforation of the walls of the cavity or vessel.

The third grasping mechanism, the snare, is probably the most widely used. Commonly, a long wire is folded in half and the folded end is passed through a catheter from its proximal end to its distal end adjacent the article to be retrieved. Once the folded end portion of the wire extends beyond the distal tip of the catheter, one of the two proximal ends of the wire is retracted to induce formation of a loop in the distal end adjacent the end of the catheter. A suitable loop usually will not form without such relative movement of the two strands of the folded wire. A permanent bend or crease is necessarily formed in the wire when it is folded. When it protrudes beyond the distal tip of the catheter, the fold remains and inhibits the wire from expanding into a loop in the absence of relative axial movement of one wire strand with respect to the other.

Once a loop has been formed, the foreign body fragment may be ensnared within the loop. Repeated passes at a free end of the fragment frequently must be attempted before the loop passes over the fragment. Successful engagement is indicated by movement of the fragment, usually viewed with fluoroscopic equipment Once engagement has been accomplished, the foreign article is pinned between the loop and the distal tip of the catheter. This may be performed by either (1) retracting one strand of the folded wire, making the loop smaller, or (2) relative movement between the entire wire and the catheter, usually by advancing the catheter over the wire until it closely contacts the ensnared body. The entire system, including the item to be retrieved, may then be retracted while engagement of the item against the catheter tip is maintained.

The snare technique is often rather difficult to utilize successfully, however. The wires used are commonly standard guide wires formed of stainless steel or like metals, which have a tendency to kink, particularly if smaller diameter wires are used. Such thin wires are necessary in many applications, however, because a double thickness of the wire must be passed through the inner lumen of the catheter and the diameter of the catheter is limited by the size of the vessels through which it is guided. This requirement of small diameter wires decreases stiffness, and hence controllable maneuverability, of the wire. Lower maneuverability limits utility in accessing remotely located fragments and makes it more difficult to control the loop when attempting to pass the loop over a portion of the foreign body fragment.

Snares known in the art suffer another deficiency as well. The loop that is formed at the tip necessarily lies in a plane parallel to the catheter. Unless a free end of the foreign body fragment happens to be substantially perpendicular to the plane of the loop, slipping the loop over the fragment may require many passes at the item. If this is unsuccessful, the physician ma have to resort to prodding the item to reorient the free end into a more acceptable position. While this may work in larger cavities where there is room to maneuver, the position of the loop may be problematic if the fragment has traveled to a remote site within a vessel where movement is much more limited.

Attempts have been made to avoid these problems. The basket mentioned above has been suggested as superior in some instances because the multiplicity of wires with slightly varying orientations ma increase the chance of grabbing the fragment. At least one researcher has attempted to solve this by providing a loop which extends to the side of a central, straight guide wire. (See Bloomfield, "The Non-Surgical Retrieval Of Intracardiac Foreign Bodies An International Survey," *Catheterization And Cardiovascular Diagnosis*, 4 (1978), 1-14.) This instrument incorporates a standard guide wire and catheter with a loose nylon thread carried on one side of the catheter. The thread is attached at two points along the exterior of the catheter, forming a loop which hangs to the side of the apparatus. This device has rather limited use due to the lack of control over the slack nylon loop and the inability to cinch the loop to tightly grip the fragment, which can severely hamper retraction. Also, use in more confined locations is limited because the catheter must be able to pass alongside an end of the article before the loop may be slipped over the end.

SUMMARY OF THE INVENTION

The invention provides a snare having an elongate proximal member and a distal segment carried adjacent the distal end of the proximal member. The distal segment is in the shape of a loop oriented at an angle to the adjacent portion of the proximal member. The proximal member desirably comprises two segments of the wire which forms the distal segment, which may be bonded to one another. An exterior sheath may also be carried around this unified wire construction to reduce friction with the catheter. The wire is formed of a shape memory material, such as a superelastic nickel-titanium alloy. The ability of such materials to resist kinking is superior to that of stainless steel of the same dimension. The superelastic shape memory property of the material allows the wire segments defining the distal segment to be straightened and collapsed upon one another into an elastically deformed configuration to pass through the lumen of a catheter and yet to automatically open into the original, unrestrained configuration upon emerging from the distal tip of the catheter.

The loop formed in the distal segment bends away from the axis of the adjacent portion of the proximal member so as to present the open loop to a fragment positioned axially forward of the catheter. Preferably the loop is formed to lie in a plane intersecting the axis of the proximal member, and desirably the plane may be substantially perpendicular to that axis. This presents a greater area of the loop toward the item being retrieved, making it much easier to pass the loop over a free end of the item. Standard guide wire materials do not permit such a construction because the wire would undergo plastic deformation when straightened for passage through the catheter. However, the use of a shape memory alloy allows the loop to be formed at an angle to the proximal member and the loop will return to this position once it exits the catheter The distal segment may also be provided with a narrow distal tip portion. This tip portion is narrower than the loop, making it easier to insert the device into a catheter.

DESCRIPTION OF THE DRAWINGS

FIG. 3 is a perspective view of a snare of the invention showing how it may be used in grasping a foreign body; and FIG. 4 is a side view of an alternative embodiment of the invention.

DETAILED DESCRIPTION OF THE INVENTION

Figure 1A:
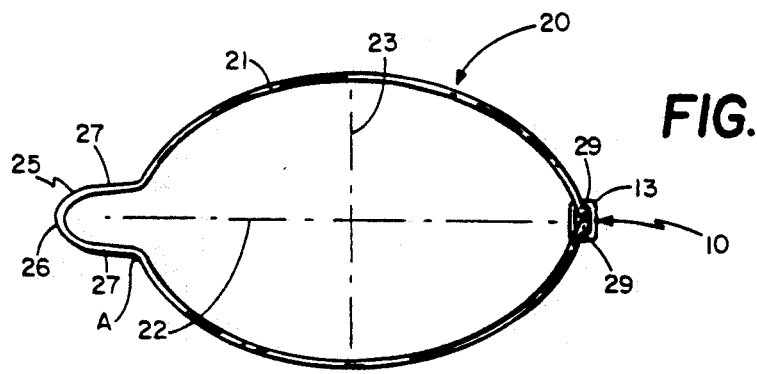
FIG. 1a is a top view of a snare according to the invention.
Figure 1B:
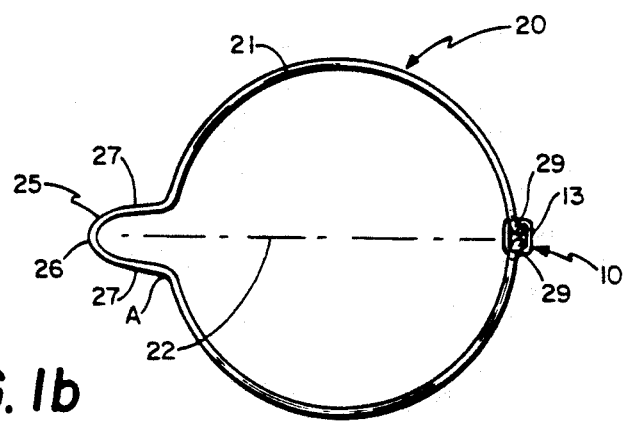
FIG. 1b is a top view of a snare according to an alternative embodiment of the invention.
Figure 2:
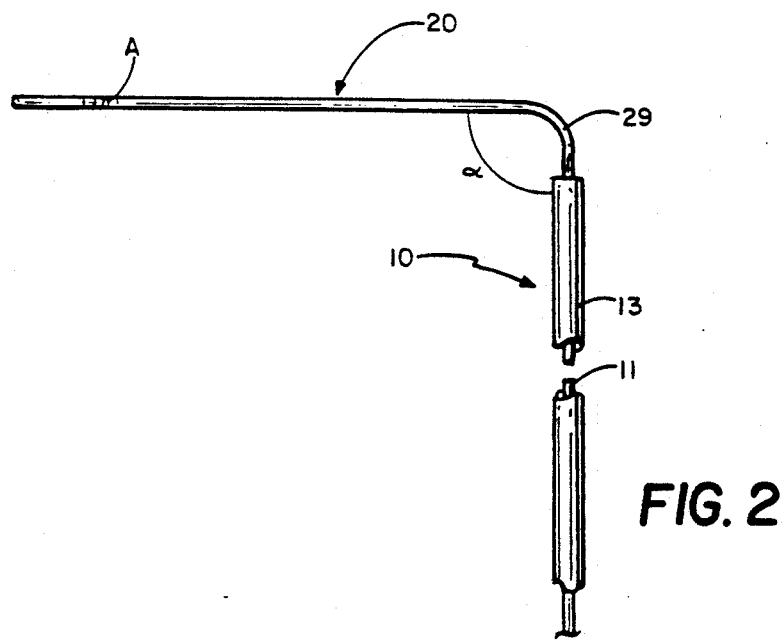
FIG. 2 is a side view of the snare of FIG. 1.

FIGS. 1 and 2 show top and side views, respectively, of a snare of the invention. The snare includes a proximal member (10) and a distal segment (20). The distal segment includes a loop formed of a superelastic alloy wire. Although the loop may be of any useful shape, it is desirably generally either circular or eliptical in shape, as shown in FIGS. 1a and b Preferably, the axis (22) of the loop is not parallel to the axis of the adjacent portion of proximal member (10) and, in a preferred embodiment, it is substantially perpendicular thereto. When the loop is deformed and inserted into the proximal end of a catheter, this axis will generally coincide with the axis of the proximal member.

Adjacent the ends of the loop, the two sides of the loop gradually taper away from the axis (22). This makes initial insertion of the device into a catheter easier than if the two sides of the loop diverged from one another more sharply. As the device is entered into the lumen of the catheter, once a small portion of the loop has entered the lumen, the catheter walls will easily collapse the rest of the loop about the axis (22) so that the two sides of the loop are held close to one another within the catheter lumen.

In a preferred embodiment, the distal segment includes a distal tip (25) which facilitates entry of the loop into the proximal end of a catheter. Desirably, the tip includes a generally U-shaped arch (26) at its distal end with each leg (27) extending rearwardly toward the loop from a side of the arch. These legs may be substantially parallel, as shown, or they may taper slightly away from one another. Although the legs could also taper toward one another away from the arch without any significant loss in utility, this embodiment is generally not preferred because then the transition from the tip to the loop is more abrupt. Desirably, this transition is fairly gradual, with the legs of the tip meeting the respective sides of the loop at an obtuse angle as shown at A in FIGS. 1a and b. This makes insertion of the snare into the catheter easier because there is no sharp bend in the wire to impede entry.

The loop and the distal tip desirably lie generally flat in a single plane, as shown, but the major axis of the loop may instead be curved. If such a curved configuration is utilized, it is preferred the apex of the curve be disposed away from the proximal end of the device, as shown in FIG. 4.

In the substantially planar embodiment illustrated in FIGS. 1a and b and FIG. 2, the axis of the proximal member (10) meets the plane containing the loop at an angle alpha which is desirably no less than about 45° nor more than about 135°, and preferably between about 90° and about 135°. An angle of about 90° is particularly preferred because this presents the full area of the loop in a distal direction, greatly enhancing the ability to slip the loop over an end of the foreign body to be retrieved. Although an angle of less than 90° may be used, grasping an article within the loop may be more difficult because the loop must pass through a greater angle as it is retracted back into the catheter to grasp the item. This angle alpha is provided between the loop and the proximal segment by forming bends (29) in the wire (21) of the loop at a position adjacent the distal end of the proximal member. These bends are desirably generally rounded, yet provide the desired angle in a relatively short distance.

The proximal member (10) comprises a single, elongate member which extends proximally from these bends and is secured thereto. In a preferred embodiment, the proximal member comprises two parallel wire segments (11), best seen in FIG. 3, that are gripped together, or bonded to, one another. Desirably, these two wire segments are extensions of the single wire (21) defining the loop. The two wires may be bonded or gripped together by any convenient means to avoid relative axial movement therebetween. Inasmuch as shape memory alloys are often relatively difficult to braze or solder, an organic adhesive, such as an epoxy resin, is preferred.

The proximal member may also include an outer sheath (13) carried about these two wire segments to reduce friction between the proximal member and the lumen of the catheter as the snare is passed therethrough. The sheath, which may serve to grip together the wire segments, may cover substantially the entire length of the proximal member, or it may terminate at a position spaced away from the proximal end of this member, as desired. Preferably, the wall of the sheath is very thin, e.g., on the order of about 0.002–0.010 inches in thickness, to keep the outer diameter of the entire proximal member small; this allows use of the invention with catheters of smaller inner diameter and permits access to smaller vessels within a patient's body. Shrink wrap tubing of polytetrafluoroethylene or the like may be employed to form the sheath. After the wires (11) are passed through the shrink wrap tubing, the tubing may be heated to cause it to shrink into tight engagement with the wire segments.

In an alternative embodiment shown in FIG. 4, the wire segments (11) of the proximal member are intertwined or twisted about one another. The wire segments may be placed next to one another and, with one end fixed, the pair of wires may be twisted about the center line of the pair. This will produce a substantially helical structure with one wire wrapped about the other, much like a common piece of yarn or twine. The two segments may then be bonded together if desired and shrink wrapped as described above. This structure increases the stiffness of the proximal portion, adding greater resistance to kinking. In most applications, this will not be necessary, however, because wires of shape memory materials, such as NiTi alloys, exhibit kink resistance significantly greater than that of stainless steel and other common guide wire materials. An intertwined configuration could not be used with the stainless steel snare designs described earlier because the two halves of the folded stainless steel guide wire generally must be able to slide with respect to one another to form the loop after passing through the catheter.

In another embodiment, a snare of the invention may incorporate an additional wire or wires in at least a portion of the proximal segment to increase stiffness. The extra wires may be used in either the straight embodiment or the intertwined embodiment of the proximal segment. Desirably, these additional wires are not incorporated in the loop portion, however. Alternatively, thicker NiTi wire may be used and the portion of the wire forming the loop may have a smaller cross sectional area than the rest of the wire. This provides a stiffer proximal segment and a flexible loop, all formed of a single wire. The segment of the wire forming the loop may be ground to a smaller diameter by any known means, such as by centerless grinding.

In yet another embodiment of the instant invention, only a distal portion of the proximal member (10) includes the paired wire segments formed from the wire (21) of the loop. The rest of the length of the proximal member may comprise any common guide wire construction, such as a single stainless steel or shape memory alloy wire. This proximal portion is attached to the distal portion of the member by known means, such as soldering, mechanical linkages, or organic adhesives. Desirably a sheath is carried over the entire length of the member, as above, covering the joint between the distal and proximal portions. The procedure in which a snare of the invention is being used will, to a certain extent, dictate the required dimensions of the device. Typically, however, the required dimensions of the instrument will fall within certain ranges. Desirably, the axis (22) of the loop is between about 0.5 cm and about 5 cm and if an eliptical loop is employed, the minor axis (23) is between about 0.3 cm and about 4.5 cm. The distal tip segment (25) will generally be about 0.5 mm to about 3 mm in length, with about 3 mm being preferred for most configurations to ensure a sufficient length to allow easy insertion into the catheter. In a particularly preferred embodiment useful in widely varying applications, the loop is substantially circular in shape with a diameter of about 1.5 cm and a distal tip about 1.7 mm long.

The wire used is desirably between about 5 mils (0.005") and about 25 mils (0.025") in diameter. Thus, the proximal member, when composed of 2 wire stands, is generally oblong in cross section with a width of at least about 10 mils, or twice the diameter of each individual wire segment. Although larger diameter wires may be used, this will necessitate the use of a catheter with a larger diameter. Employing a larger catheter in turn limits the size of the vessel through which the catheter and the snare may pass. This limitation may be of little importance for retrieving fragments from larger cavities, but when objects flow through the vascular system to remote locations and become lodged in smaller vessels, this limitation can be critical.

In an alternative embodiment, the wire used may be a cable rather than a single monofilament wire. In one configuration, the cable consists of a plurality of thin NiTi alloy wire strands twisted about one another. For example, six or more strands of NiTi wire with diameters of about 3 to 4 mils (0.003"–0.004") may be used to form the single cabled wire. In another configuration, a tungsten coil is carried about a thin monofilament NiTi core wire. Coil/core wire combinations utilizing stainless steel and like metals are well known in the art. However, the use of a core wire formed of NiTi rather than a non shape memory material provides the resulting cable with the desired shape memory properties while enhancing X-ray visibility to assist the operator in the process of guiding the snare. These cable configurations produce a distal segment which is more flexible than the monofilament embodiment, reducing trauma to the patient's tissues. This increased flexibility also makes retraction of the distal segment back into the catheter easier by providing a loop which collapses more readily. In a particularly preferred embodiment, only the loop is formed of such a coil/core wire combination; the proximal segment comprises a single monofilament NiTi wire and the two components are joined as described above.

The sheath provided on the proximal member is desirably kept very thin. For example, if polytetrafluoroethylene shrink wrap tubing is employed, tubing of wall thickness of about 2 mils, which is commercially available, may be used. This results in a proximal member with a maximum cross sectional dimension of about 32 mils if 14 mil wire is utilized Such a snare can easily be used with catheters that accept a 35 mil wire, a standard guide wire dimension. The length of the proximal member may be varied as desired for any given application, but lengths of about 60 cm to about 260 cm are preferred for most situations.

As noted above, the wire incorporated in the invention is formed of a shape memory material. Most shape memory materials known in the art today are metal alloys and the nickel titanium system is probably the best understood and most widely used of these alloys. NiTi alloys are well known in the art and need not be discussed at length here.

Many shape memory materials, including NiTi alloys, share one property in common—an ability to return to an initial configuration after being deformed. These materials are said to "remember" their previous shape. Use of such materials in the instant device allows the distal segment to be collapsed and bent to pass through the catheter, yet recapture its previous shape upon emerging from the catheter. Materials commonly used in snares known in the prior art, such as stainless steel, do not possess this shape memory property. Once they are deformed to pass through the catheter, they do not fully regain to their original shape. Thus, a snare of the invention could not be formed from such materials and still regain their unique utilitarian shape after exiting the catheter.

Shape memory alloys commonly must be subjected to a special heat treatment to define the desired "remembered" shape. When forming the present device, wire made of NiTi alloy, for example, is first shaped into the desired configuration. The wires may then be placed in an annealing oven or the like for heat treatment, as known in the art. The heat treatment process sets the shape held during heat treatment as the preferred configuration for the wire. Although NiTi alloys may be elastically deformed after heat treatment, they are extremely difficult to permanently deform, always returning substantially to their initial configuration. The proximal member of the snare may then be produced from one of these heat treated wires as outlined above, such as by bonding the two wire segments together and/or forming a sheath around them.

FIG. 3 depicts how the invention may be used to grasp a foreign item within a patient's body. First, the catheter (40) is inserted into the patient and guided to the desired location within the body as is well known in the art. Once the distal tip of the catheter is located near the foreign object, a snare of the invention is inserted into the proximal end of the catheter, with the distal end of the snare being inserted first. If the snare incorporates a distal tip (25), entry of the snare will be easier because this tip may be placed in the catheter more easily than a blunt end. The rest of the distal segment readily collapses into a elastically deformed configuration as it is urged into the catheter, as described above.

The snare is threaded through the catheter to its distal end. As the snare exits the catheter, the distal segment returns to its initial unrestrained configuration. After the loop forms and the bends (29) emerge from the catheter, the loop is oriented at the predetermined angle with respect to the proximal segment. This entire loop formation process may be accomplished with one hand advancing the proximal member; there is no need to devote both hands to form the loop, as required by the prior art snares wherein relative movement between the two halves of the folded guide wire is necessary to form a useful loop.

Once the distal segment emerges, the operator may attempt to pass the loop over an end of the foreign body. The orientation of the loop with respect to the catheter will greatly assist in this attempt, particularly if the object is located in a relatively confined area because a much greater area of the loop is presented toward the object. Once the loop is around a portion of the item being retrieved, as shown in FIG. 3, the loop may be closed about the item and held against the distal end of the catheter by advancing the catheter over the snare.

After the item is firmly grasped between the wire (21) of the loop and the distal end of the catheter, it may be retracted. This is accomplished by maintaining the relative position of the snare and the catheter and pulling both of these devices back toward the site of entry of the catheter. Smaller, more flexible foreign articles, such as fragments of guide wires, may often be retracted through the catheter's entry site, especially if a blunt puncture is used. This may not be possible for larger, stiffer items, such as catheter fragments, though. Instead, the article may be retracted as far as is safely practical and then surgically removed. Although this is not as desirable as complete removal through the entry site, it is almost certainly safer and less traumatic than gaining access to the object's original location surgically, such as by performing an open heart procedure.

Although most of the previous discussion refers to using the present invention in the vascular system, the present snare may also be used in gaining access to other body cavities, such as the stomach, bladder, or kidney. Although a snare of the invention is not particularly well suited for grasping small, rounded items, such as gall stones or kidney stones, it may be used to retrieve a wide range of articles with varying geometry and is extremely useful in removing elongate objects.

While a preferred embodiment of the present invention has been described, it should be understood that various changes, adaptations and modifications may be made therein without departing from the spirit of the invention and the scope of the appended claims.

What is claimed is:

1. A snare for use in grasping and retrieving articles in medical procedures comprising an elongate proximal segment and a distal segment comprising a flexible wire formed of a superelastic material, said wire defining a loop means for grasping said articles adjacent a distal portion of said proximal segment; said loop means being oriented at an angle of greater than 45° from said adjacent distal portion of the proximal segment.

2. A snare as in claim 1 wherein said loop portion is oriented at an angle of between about 90° and about 135° from said adjacent distal portion of the proximal segment.

3. A snare as in claim 1 wherein said loop portion is oriented at an angle substantially perpendicular to said distal portion of the proximal segment.

4. A snare as in claim 1 wherein said distal segment includes distal tip means for facilitating entry of the distal segment into a catheter.

5. A snare as in claim 4, wherein the distal tip means and the eliptical loop portion are formed of a single, continuous wire.

6. A snare as in claim 5 wherein said wire is between about 0.005 and about 0.025 inches in diameter.

7. A snare as in claim 4 wherein said proximal segment is between about 60 cm and about 260 cm in length and said distal segment is between about 0.5 cm and about 5.0 cm in length.

8. A snare as in claim 1, wherein the loop portion is substantially circular in shape and has a diameter of about 0.5 cm to about 5.0 cm.

9. A snare as in claim 1, wherein the loop portion is substantially eliptical in shape.

10. A snare for use in grasping and retrieving articles in medical procedures, comprising an elongate proximal segment having substantially parallel lengths of wire tightly encased in a sheath, and a distal segment comprising a shape memory alloy wire, said wire defining a loop portion adjacent a distal portion of said proximal segment, and said loop portion being oriented at an angle of greater than about 45° from said adjacent distal portion of the proximal segment.

11. A snare as in claim 10, wherein said sheath is formed of a plastic material having a coefficient of friction lower than that of the proximal segment wire.

12. A snare as in claim 11, wherein said plastic material is polytetrafluoroethylene.

13. A snare as in claim 10, wherein said shape memory alloy is a NiTi alloy.

14. A snare as in claim 10, wherein said wire segments of the proximal segment and the distal segment are formed of a continuous wire.

15. A snare as in claim 14, wherein said continuous wire comprises a cable which includes a plurality of interconnected wire strands.

16. A snare for use in grasping and retrieving articles and medical procedures, comprising an elongate proximal segment including at least two intertwined wire segments, and a distal segment comprising a flexible wire formed of a superelastic material, said wire defining a loop portion adjacent a distal portion of said proximal segment, and said loop portion being oriented at an angle of greater than about 45° from said adjacent distal portion of the proximal segment.

* * * * *